United States Patent
Spartiotis et al.

(10) Patent No.: US 11,432,782 B2
(45) Date of Patent: Sep. 6, 2022

(54) WIRELESS INTRAORAL X-RAY IMAGING SENSOR AND METHOD OF IMAGING

(71) Applicant: ATHLOS OY, Espoo (FI)

(72) Inventors: Konstantinos Spartiotis, Espoo (FI); Vasileios Grammatikakis, Sawtry (GB)

(73) Assignee: ATHLOS OY, Espoo (FI)

( * ) Notice: Subject to any disclaimer, the term of this patent is extended or adjusted under 35 U.S.C. 154(b) by 77 days.

(21) Appl. No.: 16/977,335

(22) PCT Filed: Mar. 8, 2019

(86) PCT No.: PCT/FI2019/050185
§ 371 (c)(1),
(2) Date: Sep. 1, 2020

(87) PCT Pub. No.: WO2019/175474
PCT Pub. Date: Sep. 19, 2019

(65) Prior Publication Data
US 2021/0052234 A1    Feb. 25, 2021

(30) Foreign Application Priority Data

Mar. 16, 2018  (FI) ...................................... 20187036
Mar. 20, 2018  (FI) ...................................... 20187040
Mar. 27, 2018  (FI) ...................................... 20187045

(51) Int. Cl.
*A61B 6/14*        (2006.01)
*A61B 6/00*        (2006.01)

(52) U.S. Cl.
CPC .............. *A61B 6/145* (2013.01); *A61B 6/425* (2013.01); *A61B 6/548* (2013.01); *A61B 6/563* (2013.01); *A61B 2560/0214* (2013.01)

(58) Field of Classification Search
CPC ......... A61B 6/145; A61B 6/425; A61B 6/548; A61B 6/563; A61B 2560/0214; A61B 6/4233; A61B 6/56
See application file for complete search history.

(56) References Cited

U.S. PATENT DOCUMENTS 5,434,418 A    7/1995  Schick
7,801,274 B1   9/2010  Isaksen
(Continued)

FOREIGN PATENT DOCUMENTS

DE    102 47 940 A1    4/2004
EP    3 120 775 A1     1/2017
(Continued)

OTHER PUBLICATIONS

International Search Report for PCT/FI2019/050185 dated May 29, 2019, 8 pages.
(Continued)

*Primary Examiner* — David P Porta
*Assistant Examiner* — Mamadou Faye
(74) *Attorney, Agent, or Firm* — Nixon & Vanderhye

(57) ABSTRACT

A wireless intraoral dental x-ray imaging sensor and method of use. The sensor optionally has a rechargeable battery located away from the edge of a PCB/ceramic substrate to enable encapsulation. The sensor has a compact microcontroller unit with several blocks including a radiolink, processing capacity, and a low power management system. Bit truncation and image compression take place on a readout substrate and/or on the MCU. External memory blocks allow for at least partial image storage for safety and as a backup.

19 Claims, 10 Drawing Sheets

(56) References Cited

U.S. PATENT DOCUMENTS

| | | | |
|---|---|---|---|
| 9,585,549 B1* | 3/2017 | Elazar | G06T 7/11 |
| 10,582,903 B2* | 3/2020 | Chun | H04N 5/32 |
| 10,699,163 B1* | 6/2020 | Shah | G06K 9/6289 |
| 2005/0220272 A1* | 10/2005 | Glazer | A61B 6/4233 |
| | | | 378/168 |
| 2006/0193436 A1* | 8/2006 | Schick | A61B 6/4494 |
| | | | 378/98.8 |
| 2007/0053498 A1 | 3/2007 | Mandelkern et al. | |
| 2007/0223649 A1 | 9/2007 | De Godzinsky et al. | |
| 2009/0129653 A1 | 5/2009 | Dehority et al. | |
| 2010/0040203 A1 | 2/2010 | Ayraud | |
| 2012/0076266 A1 | 3/2012 | Kim et al. | |
| 2012/0157829 A1* | 6/2012 | Boyden | A61B 6/4021 |
| | | | 600/427 |
| 2013/0077762 A1 | 3/2013 | Noguchi et al. | |
| 2014/0198901 A1 | 7/2014 | Christoff | |
| 2016/0316015 A1 | 10/2016 | Keating et al. | |
| 2017/0080249 A1* | 3/2017 | Brawn | A61N 5/103 |
| 2017/0086760 A1* | 3/2017 | Kim | A61B 6/145 |
| 2018/0064406 A1* | 3/2018 | Pascal | A61B 6/4208 |
| 2018/0070897 A1 | 3/2018 | Kravis et al. | |

FOREIGN PATENT DOCUMENTS

| | | | |
|---|---|---|---|
| EP | 3228251 | 10/2017 | |
| EP | 3228251 A2 * | 10/2017 | H04N 5/32 |

OTHER PUBLICATIONS

FI Office Action for FI20187036 dated Oct. 10, 2018, 8 pages.
FI Office Action for FI20187045 dated Oct. 25, 2018, 10 pages.
International Preliminary Report on Patentability issued in International Application No. PCT/FI2019/050185 dated Sep. 22, 2020.
Supplementary European Search Report issued in European Patent Application No. 19768499.6 dated Oct. 19, 2021.

* cited by examiner

WIRELESS INTRAORAL X-RAY IMAGING SENSOR AND METHOD OF IMAGING

CROSS-REFERENCE TO RELATED APPLICATIONS

The present application claims the priority right of previously filed Finnish patent application 20187036 filed on 16 Mar. 2018, Finnish patent application 20187040 filed on 20 Mar. 2018 and Finnish patent application 20187045 filed on 27 Mar. 2018.

FIELD OF THE INVENTION

The present invention relates to intraoral x-ray imaging sensors and more specifically to wireless intraoral imaging sensors (WIOS).

BACKGROUND OF THE INVENTION

This section illustrates useful background information without admission of any technique described herein representative of the state of the art.

Intraoral imaging utilizing sensors have the advantage of immediate (within few seconds) display on the computer screen of the diagnostic intraoral images as opposed to the use of phosphor plates which require a reader for extracting the digital image. Additionally several images can be taken one after the other to create a full mouth series. An intraoral x-ray imaging sensor has typically a detector to convert incoming x-rays to either visible light (indirect conversion) or to electric pulse (direct conversion). Examples of indirect conversion intraoral detector include cesium iodide (CsI) deposited on a fiber optic plate. Examples of direct conversion intraoral detectors include silicon (Si), cadmium telluride (CdTe) and mercuric iodide ($HgI_2$), although none of the direct conversion intraoral sensors has reached the market yet. The light in the case of the indirect conversion sensors and the electric current in the case of direct conversion intraoral sensors goes to a readout Complementary Metal Oxide Semiconductor (CMOS) substrate which either detects the light or stores the electric current. The CMOS is then readout either in analog mode or in digital mode with an analog to digital converter resident on the CMOS itself. In older versions of intraoral sensors the readout substrate was comprising a Charged Coupled Device (CCD).

The available intraoral sensors have a cable attached to the backside of an encapsulated sensor, which comes out of the mouth and is connected to a readout box further down, or to an input port of a computer. The cable carries the signals to control the electronics of the intraoral sensor and the CMOS and also carry the output of the CMOS for display to a monitor.

Additionally in some models the cable is connected nearby to a device for initial display of the image and further down streaming from the nearby device via wireless link to a main computer or other diagnostic station.

The presence of the cable coming out of the mouth is creating discomfort to the patients and makes positioning of the sensor difficult. In many cases the discomfort and the difficulty in positioning leads to faulty exposures and as a result a new exposure is required.

Additionally the cable and in particular the area where the cable comes out from the back of the sensor is one the main failure points. The connection of the cable to the backside of the sensor needs to withstand stress and strain in everyday use with pull, push and rotational forces applied to the contact. Quite often the cable close to or at the backside contact will break. As a result the connection needs to be reinforced causing a relatively large hump on the back of the sensor in all three dimensions. This large hump causes more inconvenience to the patient.

SUMMARY

It would be very desirable to have a completely wireless, compact and robust intraoral sensor.

It has been observed that a viable wireless intraoral sensor may fail for mainly the following reasons:
 The wireless sensor is powered by a single use battery that will last a few exposures and will have to be disposed afterwards. A new battery will have to be used subsequently
 A wireless link is not reliable and data is lost all too often, creating the need of additional exposure
 The sensors, although wireless, are bulky mainly due to the use of indirect conversion scintillator with a thick fiber optic plate, single use thick battery packs and bulky wireless electronics
 The sensors are fragile and sensitive. A wireless sensor is even more likely to be dropped on the floor accidentally and consequently it is even more imperative that a wireless sensor is robust and withstands shocks.

It has been observed that it would be extremely desirable and a major advancement in the field of intraoral x-ray imaging to be able to provide a completely wireless intraoral sensor, i.e. an intraoral sensor without a cable coming off the back of the sensor that is inserted to the human mouth and to mitigate the obstacles and deficiencies of the prior art. To that effect embodiments of the present invention provide a wireless intraoral x-ray imaging sensor which:
 has a rechargeable compact battery suitably positioned an adequate distance from the edge of the Printed Circuit Board (PCB) (or ceramic) to allow an encapsulation where the hump on the backside is not in contact with the edges of the sensor thus providing a comfortable and easy to position sensor.

Embodiments of the present invention also provide a wireless intraoral x-ray imaging sensor which:
 bit truncates and/or compresses the x-ray image data sufficiently to allow wireless transmission of the bit truncated and/or compressed x-ray image in ten seconds (10 sec) or less and preferably in five seconds (5 sec) or less.

Embodiments of the present invention also provide a wireless intraoral x-ray imaging sensor which:
 has an event based self-triggering scheme to wake up an on-board Micro Controller Unit (MCU) and thereby optimize battery usage In accordance with a first aspect of the invention we provide a wireless intraoral x-ray imaging sensor, comprising a radiation sensitive detector which detects impinging x-rays creating an output signal; a plurality of pixels on a readout substrate for receiving said output from detector, said readout substrate outputting x-ray image data in the form of analog or digital pixel values; a further substrate connected to said readout substrate comprising electronics for creating a wireless link for transmitting said x-ray image data to a receiving device, and a rechargeable battery for providing power to said wireless intraoral x-ray imaging sensor; characterized in that said rechargeable battery edges have a minimum distance of 2 mm from the edges of said further substrate.

In accordance with another aspect of the invention we provide a wireless intraoral x-ray imaging sensor, comprising a radiation sensitive detector which detects impinging x-rays creating an output signal; a plurality of pixels on a readout substrate for receiving said output from detector, said readout substrate outputting x-ray image data in the form of analog or digital pixel values; a further substrate connected to said readout substrate comprising electronics for creating a wireless link for transmitting said x-ray image data to a receiving device, characterized in that said readout substrate includes logic or in the alternative said electronics execute an algorithm, to send the image in parts via the wireless link to a base station or tablet or mobile phone allowing for fast image preview on a display media.

In certain embodiments, said fast image preview is available in three (3) seconds or less from the end of an exposure.

In certain embodiments, said algorithm for sending the image in parts comprises sending regularly, for example, every second, preferably every third and even more preferably every fourth row or column of the image, until all rows or columns have been sent.

In accordance with another aspect of the current invention we provide a wireless intraoral x-ray imaging sensor, comprising a radiation sensitive detector which detects impinging x-rays creating an output signal; a plurality of pixels on a readout substrate for receiving said output from detector, said readout substrate outputting x-ray image data in the form of analog or digital pixel values; a further substrate connected to said readout substrate comprising electronics for creating a wireless link for transmitting said x-ray image data to a receiving device, characterized in that said wireless intraoral x-ray imaging sensor includes a shutdown operation mode during which power block and radio block are active and running a low power duty cycle.

In certain embodiments, during the shutdown mode of operation only power block and radio block are active.

In certain embodiments, said wireless intraoral x-ray imaging sensor further comprises a rechargeable battery for providing power to said wireless intraoral x-ray imaging sensor; characterized in that said rechargeable battery edges have a minimum distance of 2 mm from the edges of said further substrate.

In certain embodiments, said readout substrate is disposed directly onto said first face of further substrate and said rechargeable battery is disposed directly onto second face opposite to first face of said further substrate.

In certain embodiments, said rechargeable battery has a cylindrical shape.

In certain embodiments, said rechargeable battery is recharged via contacts provided on the surface of said further substrate, said contacts having a height profile of less than or equal to 10 mm.

In certain embodiments, said contacts do not extend beyond the surface of the encapsulation back cover.

In certain embodiments, the readout substrate is a Complementary Metal Oxide Semiconductor ("CMOS").

In certain embodiments, said further substrate comprises a printed antenna, further described later on with reference to FIG. 1c.

In certain embodiments, said electronics comprise a MicroController Unit (MCU) which includes control electronics.

In certain embodiments, said further substrate comprises external to the microcontroller unit memory cells to store at least part of the image data.

In certain embodiments, said readout substrate includes logic to execute bit truncation or data compression.

In certain embodiments, said electronics comprise a microcontroller unit ("MCU") or a field programmable gate array ("FPGA") or a complex programmable logic device ("CPLD") or an application specific integrated circuit ("ASIC").

In certain embodiments, said microcontroller unit executes an algorithm for bit truncation or data compression.

In certain embodiments, said data compression comprises lossless data compression.

In certain embodiments, said data compression comprises lossy data compression.

In certain embodiments, said readout substrate includes event trigger cells and digital logic which upon detection of the beginning of an exposure provide a signal to activate the MCU wakeup block and wake up the MCU from a sleep state.

In certain embodiments, the current requirement while in shutdown mode is 5 mA or less, preferably 2.5 mA or less and ideally 1 mA or less.

In certain embodiments, the x-ray imaging sensor has a sleep mode operation which it enters after an x-ray exposure and transits from said sleep mode to said shutdown mode after a factory set or user-controlled timeout period following said x-ray exposure.

In certain embodiments, the x-ray imaging sensor is capable of exiting the shutdown mode and enter into said sleep mode with a command received by the x-ray imaging sensor via the wireless link.

In accordance with a second aspect of the invention we also provide a method for performing wireless intraoral x-ray imaging said method comprising:
  a) providing a wireless intraoral x-ray imaging sensor, comprising a radiation sensitive detector which detects impinging x-rays creating an output signal;
  b) providing a plurality of pixels on a readout substrate for receiving said output from detector, said readout substrate outputting x-ray image data in the form of analog or digital pixel values;
  c) providing a further substrate connected to said readout substrate comprising electronics for creating a wireless link for transmitting said x-ray image data, and a rechargeable battery for providing power to said wireless intraoral x-ray imaging sensor;
  said method being characterized in that it further includes at least two of the steps from:
  d) bit truncation of the acquired intraoral x-ray image data prior to wireless x-ray image data transmission
  e) compression of the intraoral x-ray image data prior to wireless x-ray image data transmission
  f) storing at least part of the acquired x-ray image data in a memory provided on said further substrate prior to wireless said x-ray image data transmission
  g) storing at least part of the acquired x-ray image data in a memory provided on said further substrate after wireless said x-ray image data transmission.

In accordance with another aspect of the invention we provide a wireless intraoral x-ray imaging sensor, comprising a radiation sensitive detector which detects impinging x-rays creating an output signal; a plurality of pixels on a readout substrate for receiving said output from detector, said readout substrate outputting x-ray image data in the form of analog or digital pixel values; a further substrate connected to said readout substrate comprising electronics for creating a wireless link for transmitting said x-ray image data to a receiving device, and a rechargeable battery for providing power to said wireless intraoral x-ray imaging sensor; characterized in that said rechargeable battery is recharged wirelessly. In certain embodiments, said wirelessly rechargeable battery is recharged utilizing a coil disposed on top of the battery.

In accordance with yet another aspect of the invention we provide a wireless intraoral x-ray imaging device said device comprising:
  a) a wireless intraoral x-ray imaging sensor, comprising a radiation sensitive detector which detects impinging x-rays creating an output signal;
  b) a plurality of pixels on a readout substrate for receiving said output from detector, said readout substrate outputting x-ray image data in the form of analog or digital pixel values;
  c) a further substrate connected to said readout substrate comprising electronics for creating a wireless link for transmitting said x-ray image data, and a rechargeable battery for providing power to said wireless intraoral x-ray imaging sensor;
  said wireless intraoral x-ray imaging device being characterized in that said readout substrate or said electronics execute at least two of:
  d) bit truncation of the acquired intraoral x-ray image data prior to wireless transmission of said x-ray image data
  e) compression of the intraoral x-ray image data prior to wireless transmission of said x-ray image data
  f) storing at least part of the acquired x-ray image data in a memory prior to wireless transmission of said x-ray image data
  g) storing at least part of the acquired x-ray image data in a memory after wireless transmission of said x-ray image data.

In accordance with yet another aspect of the invention we provide a wireless intraoral x-ray imaging sensor, comprising a radiation sensitive detector which detects impinging x-rays creating an output signal; a plurality of pixels on a readout substrate for receiving said output from detector, said readout substrate outputting x-ray image data in the form of analog or digital pixel values; a further substrate connected to said readout substrate comprising electronics for creating a wireless link for transmitting said x-ray image data to a receiving device, and a rechargeable battery for providing power to said wireless intraoral x-ray imaging sensor; characterized in that said further substrate comprises, external to electronics, memory cells for storing at least part of said x-ray image data.

In accordance with yet another aspect of the invention we provide a wireless intraoral x-ray imaging sensor, comprising a radiation sensitive detector which detects impinging x-rays creating an output signal; a plurality of pixels on a readout substrate for receiving said output from detector, said readout substrate outputting x-ray image data in the form of analog or digital pixel values; a further substrate connected to said readout substrate comprising electronics for creating a wireless link for transmitting said x-ray image data to a receiving device, and a rechargeable battery for providing power to said wireless intraoral x-ray imaging sensor; characterized in that said further substrate comprises a printed antenna.

In accordance with yet another aspect of the invention we provide a wireless intraoral x-ray imaging sensor, comprising a radiation sensitive detector which detects impinging x-rays creating an output signal; a plurality of pixels on a readout substrate for receiving said output from detector, said readout substrate outputting x-ray image data in the form of analog or digital pixel values; a further substrate connected to said readout substrate and comprising electronics for creating a wireless link for transmitting said x-ray image data to a receiving device, and a rechargeable battery for providing power to said wireless intraoral x-ray imaging sensor; characterized in that said electronics comprises a microcontroller unit said microcontroller unit comprising asic control access interface, asic data access interface, a microcontroller unit wakeup block and a radio block.

In accordance with yet another aspect of the invention we provide a wireless intraoral x-ray imaging sensor, comprising a radiation sensitive detector which detects impinging x-rays creating an output signal; a plurality of pixels on a readout substrate for receiving said output from detector, said readout substrate outputting x-ray image data in the form of analog or digital pixel values; a further substrate connected to said readout substrate and comprising electronics for creating a wireless link for transmitting said x-ray image data to a receiving device, and a rechargeable battery for providing power to said wireless intraoral x-ray imaging sensor; characterized in that said readout substrate or said electronics execute bit truncation or data compression of the x-ray image data prior to wireless transmission.

In accordance with yet another aspect of the invention we provide a wireless intraoral x-ray imaging sensor, comprising a radiation sensitive detector which detects impinging x-rays creating an output signal; a plurality of pixels on a readout substrate for receiving said output from detector, said readout substrate outputting x-ray image data; a further substrate connected to said readout substrate comprising electronics for creating a wireless link for transmitting said x-ray image data to a receiving device, and a rechargeable battery for providing power to said wireless intraoral x-ray imaging sensor.

In certain embodiments, the wireless intraoral sensor comprises a rechargeable battery located suitably away from the edge of a PCB/ceramic substrate to enable encapsulation whereby a hump on the back side of the sensor is not touching the edge. In certain embodiments, a microcontroller unit, MCU, is of the type that has several blocks including a radio link, processing capacity and a low power management system incorporated therein, thus making the overall structure compact. In certain embodiments, bit truncation and image compression take place on a readout substrate and/or on the MCU. In certain embodiments, external memory blocks allow for at least partial image storage for safety and as a backup.

Different non-binding example aspects and embodiments have been presented in the foregoing. The above embodiments and embodiments described later in this description are used to explain selected aspects or steps that may be utilized in implementations of the present invention. It should be appreciated that corresponding embodiments apply to other example aspects as well. Any appropriate combinations of the embodiments can be formed.

BRIEF DESCRIPTION OF THE DRAWINGS

In the following, the invention is presented in detail by referring to the attached drawings, where.

DETAILED DESCRIPTION

With reference now to the accompanying figures we describe in detail the invention and the preferred embodiments.

Figure 1A:
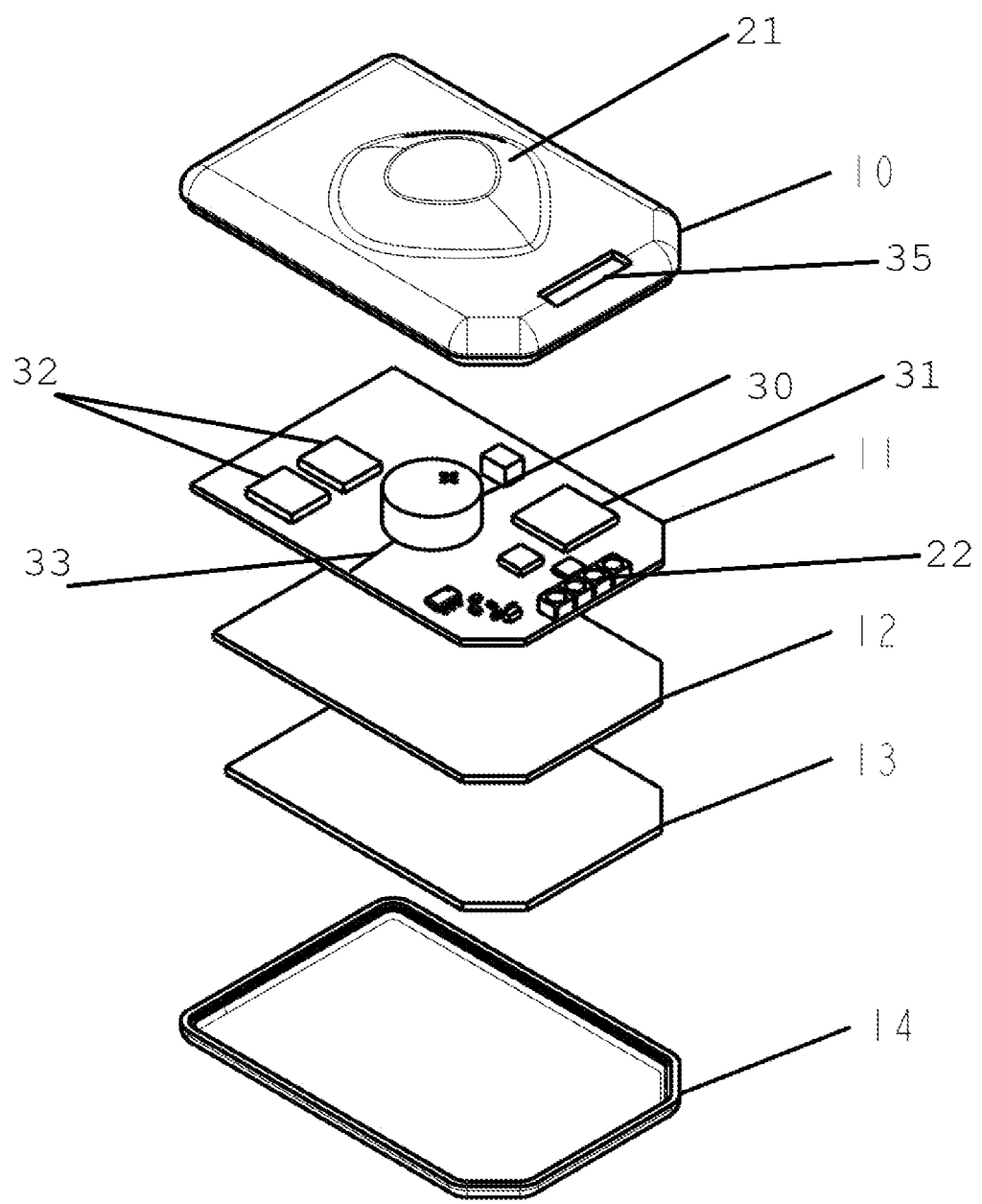
FIG. 1a shows a blow up view of the wireless direct conversion Silicon based intraoral sensor in accordance with certain embodiments.

With reference now to FIG. 1a a direct conversion wireless intraoral sensor comprises a Silicon (Si) direct conversion semiconductor detector substrate 13 bonded to a readout substrate 12 which is an Application Specific Integrated Circuit (ASIC). Typically such readout ASIC substrates comprise Complementary Metal Oxide Semiconductor (CMOS) configured to accumulate the electric charge generated inside the direct conversion detector substrate 13 in response to impinging x-rays, onto a charge accumulating capacitance prior to reading out. The charge accumulating capacitance is provided on each pixel and the charge value is readout pixel by pixel and optionally converted to a digital pixel value on the CMOS prior to readout. The Si-CMOS hybrid has an active area sensitive to incoming x-rays. In dental intraoral x-ray imaging there are worldwide three different active area sensors, independently to what is the detector material or detection technique. The three different intraoral sensor categories are: a) size 0 with active area 15-18 mm×20-24 mm, b) size 1 with active area 19-23 mm×28-32 mm and c) size 2 with active area 24-27 mm×33-36 mm.

With reference to FIG. 1a, the Si-CMOS is glued and wire bonded onto a further substrate 11 (otherwise referred to hereinafter also as electronics substrate) which is typically a Printed Circuit Board (PCB) made of FR4 multilayers or in the alternative a ceramic type of further substrate. The backside of the CMOS readout substrate 12 is directly disposed onto the first face of electronics substrate 11 without any intermediate or other substrates in between. This is an important aspect of certain embodiments of the invention as any intermediate substrates would add thickness to the sensor overall structure and thickness translates to discomfort when placed inside the mouth. The electronics substrate 11 carries, on the opposite face to the one where the Si-CMOS hybrid is mounted, all the external/peripheral components needed to control and readout the CMOS 12. In accordance with certain embodiments it comprises a Microcontroller Unit (MCU) 31, and in accordance with certain embodiments external memory cells 32 with sufficient capacity to hold a full post processed image. In accordance with certain embodiments the further substrate 11 also contains a battery 30 directly disposed thereon on the same face containing the external and peripheral components. This makes the structure compact since intermediate substrates that would otherwise add thickness to the sensor are explicitly avoided. The battery is rechargeable and having a capacity of 5 mAh or more, preferably a capacity between 5 mAh-50 mAh and ideally a capacity between 15 mAh to 25 mAh to be able to provide sufficient energy but also be compact. The operating voltage of the rechargeable battery 30 is between 2.5 Volts and 5 Volts. In accordance with certain embodiments the rechargeable battery 30 must have a lifetime of at least 50 cycles, more preferably 100 cycles and most preferably 300 cycles or more. The rechargeable battery 30 should be of an appropriate shape that allows compact encapsulation, without adding thickness to the sensor throughout. For patient comfort it is critical that post encapsulation the hump due to the battery is as localized as possible and as thin as possible. In accordance with certain embodiments furthermore after the encapsulation, the hump on the back of the wireless intraoral sensor is not too close to the edge of the sensor as this would cause discomfort and make positioning harder. In accordance with certain embodiments the rechargeable battery 30 is of a cylindrical shape with a diameter of 15 mm or less and height of 8 mm or less. More preferably the rechargeable battery 30 is of cylindrical shape and has diameter of 10 mm or less and height of 6 mm or less. Furthermore the layout of the further substrate 11 containing thereon the external electronics (including the MCU, memory etc) and peripherals is such that allows the positioning 33 of the battery 30 to be at least 2 mm, better at least 3 mm to 5 mm and even better at least 7 mm inwards from the nearest edge 33 of the further substrate 11. With this electromechanical arrangement the backside of the encapsulation 10 will have a hump 21 which is ideally centered in the short dimension or at least not reaching the edge of the encapsulation cover 10. As said this is critical and improves dramatically patient comfort and makes positioning of the sensor inside the mouth easier.

In certain embodiments the PCB substrate 11 provides for electrical contacts 22 to allow recharging of the battery but also allow for electronic communication with the MCU 31 and the memory cells 32. The contacts 22 are preferably flat on the surface of the PCB 11 and with a profile height that post encapsulation (10, 15) the contacts 22 are flush to the encapsulation surface and do not extend beyond the opening 35 of the backside cover (10, 15) by more than 5 mm, preferably contacts 22 extend less than 3 mm and even more preferably contacts 22 have post encapsulation the same profile height as the opening 35 of backside cover (10, 15), i.e. they do not cause any unevenness on the encapsulation surface. In FIG. 1a, the direct conversion detector 13 can be instead of Si a different semiconductor, as for example CdTe, CdZnTe, HgI2, PbI2, Ge, GaAs or a perovskite without departing from the teachings of the invention and/or its embodiments. In front of the semiconductor direct conversion detector 13 there is the front cover 14 of the encapsulation, otherwise also referred to as also the x-ray window.

Figure 1B:
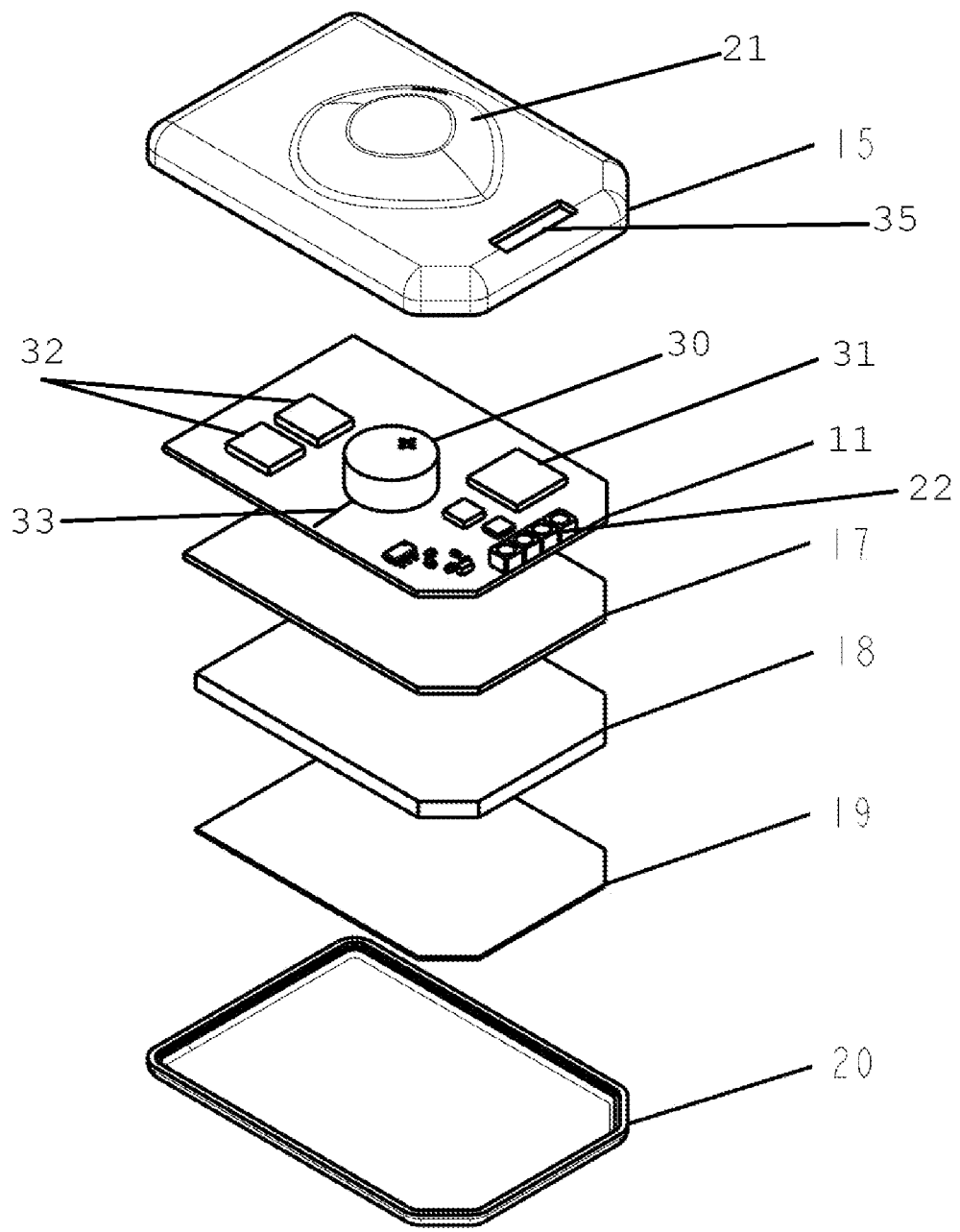
FIG. 1b shows a blow up view of the wireless indirect conversion scintillator based intraoral sensor in accordance with certain embodiments.

With reference to FIG. 1b, all teachings of the invention and/or its embodiments apply equally as described with reference to FIG. 1a. The difference in FIG. 1b is that this is a sensor of indirect conversion type. Indirect conversion x-ray substrate 19 is a scintillator for example CsI or a phosphorous plate. Attached to scintillator substrate 19 is a fiber optic plate 18 which guides the generated light inside the CsI substrate 19 to the readout substrate 17. Fiber optic plate 18 also acts as a shield for unabsorbed x-rays. The CMOS (readout) substrate 17 is at least partially different from CMOS (readout) substrate 12 of the direct conversion type in at least the functionality of the pixels which in the case of indirect conversion CMOS readout substrate 17 must include also a photodiode (on each pixel) to detect the incoming light and convert it to an electronic signal. Otherwise all other functionalities described for the readout substrate CMOS 12 in the direct conversion case of FIG. 1a, apply also in the case of FIG. 1b, and the inventive features and teachings described with reference to FIG. 1a apply to the case of indirect conversion of FIG. 1b. Specifically the readout substrate 17 is directly disposed onto a first face of the electronics substrate 11 without any intermediate or additional substrates. The battery 30 is directly disposed on the opposite face of the electronics substrate 11 and as stated for FIG. 1a, it is of cylindrical shape and has diameter of 10 mm or less and height of 6 mm or less. Furthermore, the layout of the further substrate 11 containing thereon the external electronics (including the MCU, memory etc) and peripherals is such that allows the positioning 33 of the battery 30 to be at least 2 mm, better at least 3 mm to 5 mm and even better at least 7 mm inwards from the nearest edge 33 of the further substrate 11.

Figure 1C:
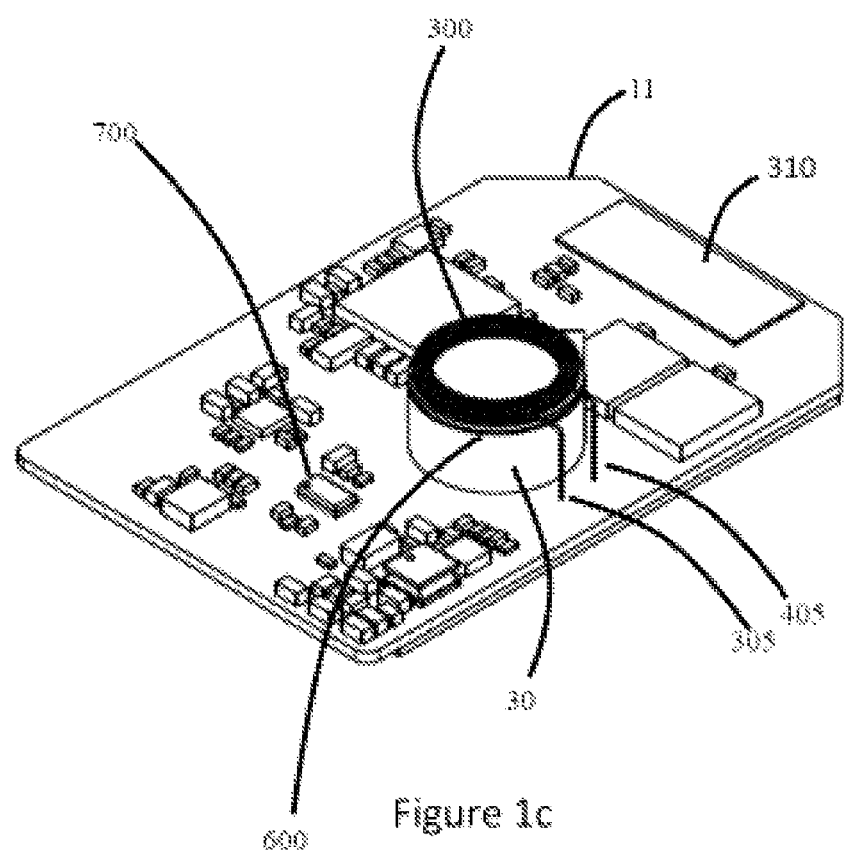
FIG. 1c shows an x, y view of the further substrate of FIGS. 1a and 1b in a wireless intraoral sensor containing the printed antenna, cylindrical rechargeable battery and wireless recharging receiver coil.

With reference to FIG. 1c we show and x, y view of the further substrate 11 (of FIGS. 1a and 1b) comprising electronics, adequate for creating a wireless link and transmitting said image data. Further substrate 11 contains the rechargeable battery 30 for providing power to said wireless intraoral x-ray imaging sensor and is characterized in that said rechargeable battery 30 has a minimum distance 33 of two millimetres (2 mm) from the edges of the substrate 11. In accordance with certain embodiments the antenna 310 is of the printed antenna type and is positioned suitably close to one edge of the further substrate 11. The further substrate 11 typically is a printed circuit board (PCB), for example one made of FR4 material and under the printed antenna 310 the PCB does not contain any conductive tracks or metal layers in order to maximize the antenna performance. For example suitable position of the antenna 310 is across from the PCB end where the readout substrate is wire bonded to the PCB and where usually the corners of the further substrate 11 are truncated.

In certain embodiments the rechargeable battery 30 has cylindrical shape.

In certain embodiments said rechargeable battery 30 is recharged wirelessly via a receiver coil 300 disposed on top of the battery 30. Preferably the receiver coil 300 is disposed on a thin adhesive insulating substrate 600, preferably in the form of a tape, so that it can be attached on top of the battery 30 in order to minimize space occupancy. Receiver coil 300 is connected to the substrate 11 through its two ends (305, 405) and thereto an integrated circuit 700 that performs all the necessary functions to safely recharge the battery 300. As noted from FIG. 1c the recharging connector 22 of FIGS. 1a & b, is no longer needed and is not present in the embodiment of FIG. 1c. Instead the space taken in the previous embodiments of FIGS. 1a & b by connector 22, is now taken by the printed antenna 310. In FIGS. 1a and 1b the printed antenna 310 occupies a different part of the substrate 11, for example on the upper right corner where space is available (not shown). It should be noted that a printed antenna is an antenna that is incorporated as part of the PCB as opposed to a surface mounted antenna that is a discrete component mounted on the PCB. Although a printed antenna on occasion may have a smaller wireless link budget than a dedicated discrete antenna, or it is difficult to tune and optimize it is chosen in certain embodiments due to the fact it is compact and occupies very small space. It should also be noted that a printed antenna is not an inherent part of a PCB, but in accordance with certain embodiments the PCB, i.e. the further substrate 11 where external electronics and peripherals are discreetly mounted, must be specifically designed to include a printed antenna and a printed antenna design is diligently tuned to be effective.

The receiver coil 300 structure is characterized as having sufficient inductance and area to effectively couple to a corresponding wireless power transmitter situated in the base station 5. The wireless transmitter is generating an alternating magnetic field which couples over a gap typically 3 to 5 mm and induces a current in the receiver coil 300. This AC current is then rectified and filtered so that it can be used to charge the rechargeable battery 30 through the charger integrated circuit 700. Integrated circuit 700 performs several functions such as the charging function of the battery 30, protection for battery 30 from under voltage and overvoltage, power management etc.

Figure 4:
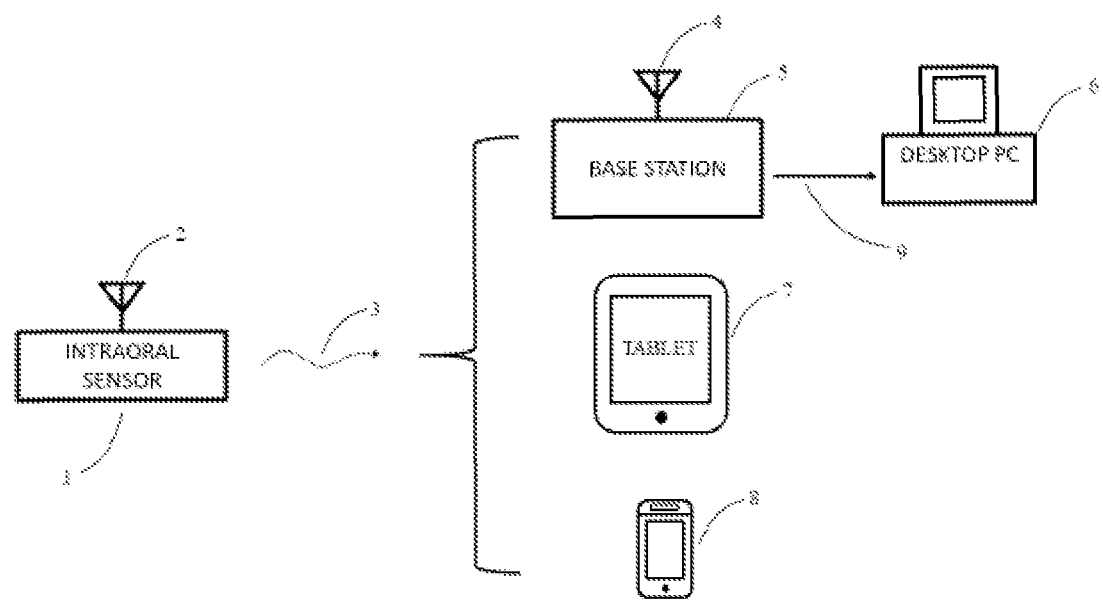
FIG. 4 shows a functional general block diagram, of a wireless intraoral sensor system in accordance with certain embodiments.
Figure 4A:
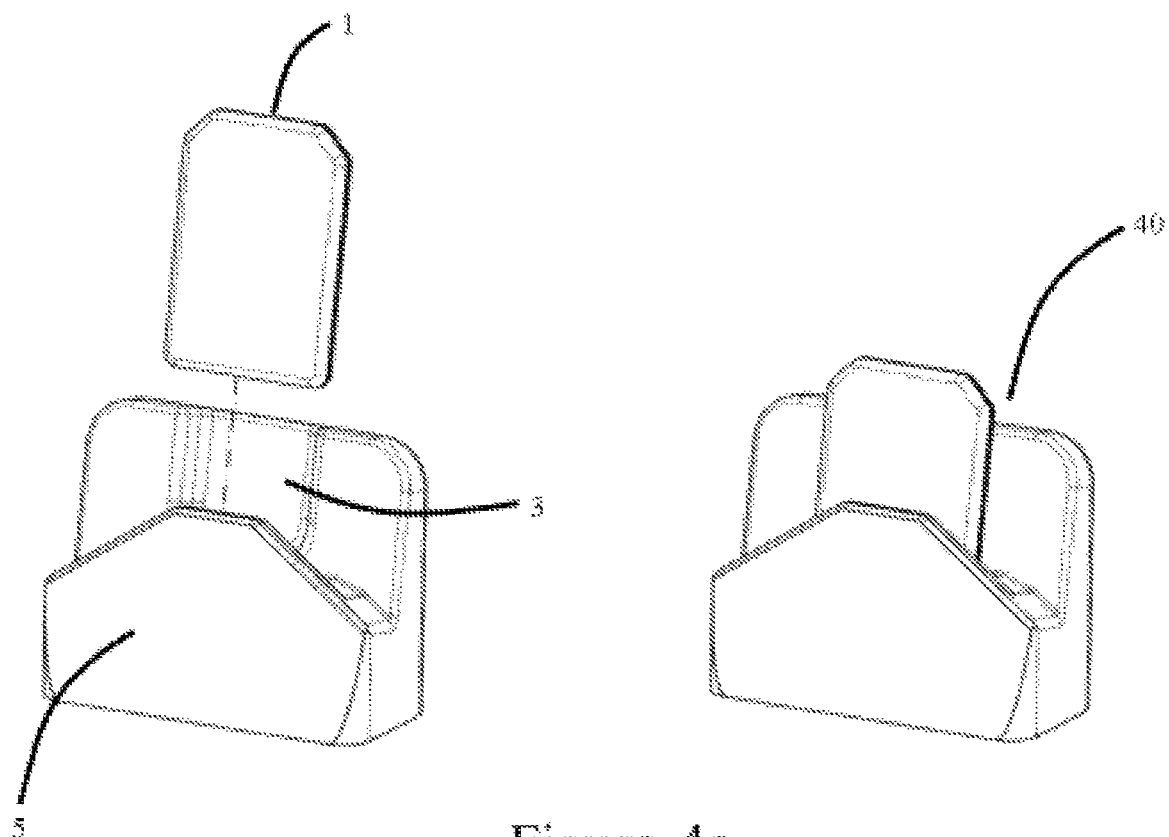
FIG. 4a shows the base station and the wireless intraoral sensor inserted in the base station for wireless recharging of the battery.

Turning to the base station 5 we show an exemplary embodiment in FIG. 4a. Certain embodiments are provided with the ability of the base station 5 to charge the sensor 1 wirelessly. The base station 5 features a wireless power transmitter by means of a power transmission coil and related control electronics located inside its mechanical enclosure behind wall 3. When the user requires to recharge the sensor 1, the latter is placed inside a properly formed cavity 40 of the base station 5 so that the power transmission coil of the base station 5 and the power reception coil 300 of the sensor 1 are aligned. When this event occurs power transmission and reception begin and is being controlled by the base station 5 until the sensor 1 battery 30 is fully charged or the user removes the sensor 1 from the base station 5.

Figure 2:
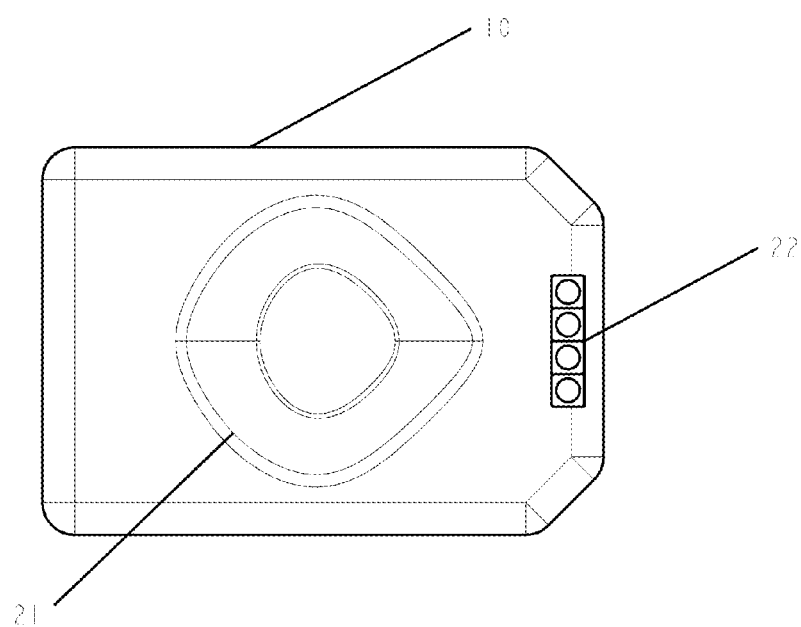
FIG. 2 shows an x-y view of the backside of the wireless intraoral sensor in accordance with certain embodiments.

With reference to FIG. 2 the present invention and/or its embodiments is exemplified. In FIG. 2 the backside 10 of the encapsulated wireless direct conversion intraoral sensor of FIG. 1a is shown. The hump 21 encapsulating the rechargeable battery 30 is not extending all the way to the edge of the encapsulation 10 due to the appropriate design and placement of the battery 30 on the PCB 11 as described earlier herewith. Recharging and electronic communication contacts 22 do not extend beyond the surface of the backside surface 10 of the encapsulation, i.e. they are flush to the encapsulation face thus providing for a smooth encapsulation face.

Figure 3:
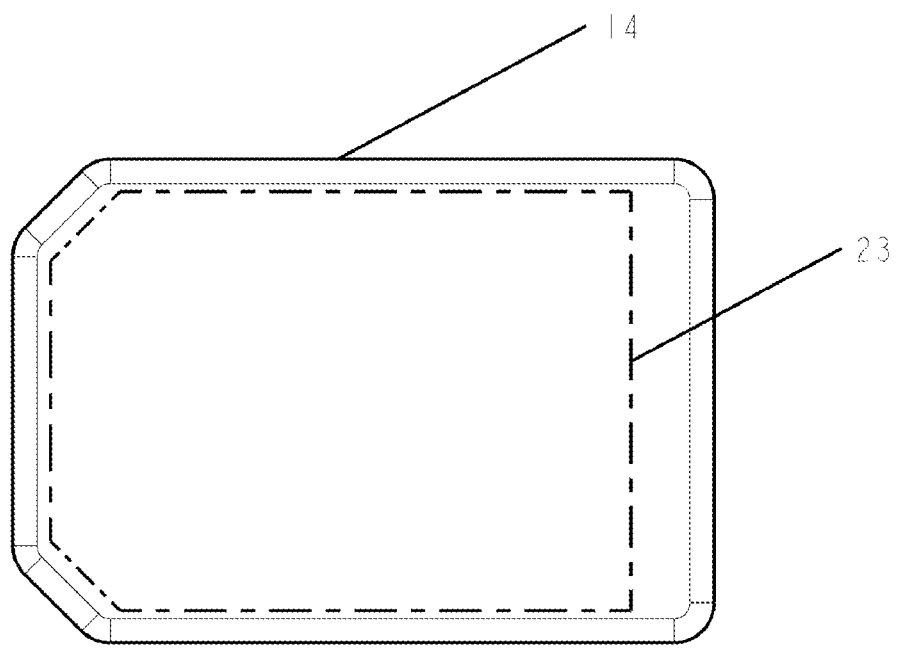
FIG. 3 shows an x-y view of the front side (incident x-rays direction) of the wireless intraoral sensor in accordance with certain embodiments.

With reference to FIG. 3 the front side 14 of the encapsulated wireless intraoral sensor is shown where the active area 23 is also shown. Under the active area 23 the pixel array of the readout substrate (12, 17) (CMOS) is positioned.

With reference to FIG. 4 an intraoral sensor 1 comprises a transceiver 2 for wirelessly transmitting x-ray image data 3. The receiving end maybe a base station 5 including a receiver 4. The base station sends the x-ray image data for display to a personal computer (PC) 6 including a monitor via a wired or wireless link 9. The link between the base station and the PC can be for example a USB 2.0 or a USB 3.0 in the case of wired link or can be a high bandwidth wireless Wi-Fi connection. In the alternative the x-ray image data 3 may be received directly into a tablet 7 or a mobile device 8, for example a phone.

Figure 5:
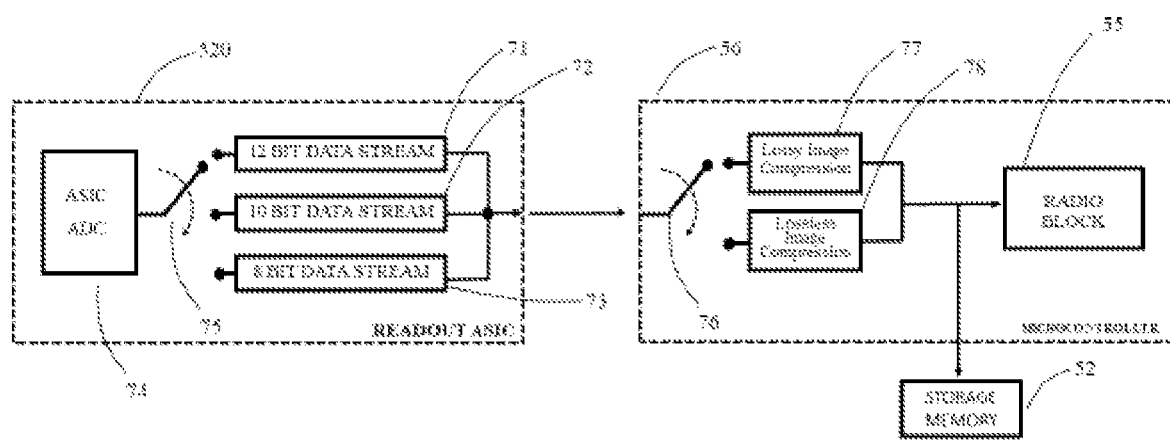
FIG. 5 shows a functional block diagram, including bit truncation, data compression, memory storage and data transmission, of the wireless intraoral sensor in accordance with certain embodiments.

With reference to FIG. 5 the readout substrate 12 of FIG. 1a is a readout Application Specific Integrated Circuit (ASIC) 520. Commonly the readout ASIC 520 comprises a Complementary Metal Oxide Semiconductor (CMOS). The readout ASIC 520 includes an Analog to Digital Converter (ADC) 74 which digitizes the analog signal. Typically for intraoral sensors one would use a 12 bit ADC. However in accordance with certain embodiments a 12 bit on chip ADC would produce quite a significant amount of data which would slow down the wireless transmission of the image. By way of example a size 2 intraoral sensor may contain an array of pixels 1000×1400, i.e. 1.4 Mpixels. At 12 bits per pixel the size of the x-ray image would be 2.1 MBytes. For low power consumption wireless transceivers with limited bandwidth this constitutes a significant amount of data. Currently, some of the fastest but also low power consumption and wireless transceivers could emit at 200 kByte/second. At this rate it would take 10.5 seconds to transmit the x-ray image data. This would not be acceptable from a workflow standpoint, especially when the doctor wants to execute a full mouth series with 15 or more x-rays taken. In certain embodiments the readout ASIC 520 contain after the ADC a stage whereby one or more of the least significant bits are truncated. This on-chip (i.e. on the readout substrate 12 of FIG. 1a or 17 in FIG. 1b) truncation may reduce the number of bits output from the readout substrate selectively 75 from 12 bits 71 to for example 10 bits 72 or even 8 bits 73. Selectively and at the expense of some extra transmission time the original 12 bits 71 can be maintained and transmitted. Certain embodiments therefore provide for a simple and practical approach to shorten the wireless transmission time of the x-ray image data. With 8 bits 73 in the above example the x-ray image size becomes 1.4 MBytes which at 200 kByte/sec would mean a 7 second transmission time, already a significant improvement. On most computer monitors and in most practical cases 8 bits of image resolution would offer more than enough grey scales and dynamic range for clinical diagnosis.

Still with reference to FIG. 5, the bit truncated x-ray image is then received on the further substrate 11 of FIG. 1a, containing a Micro Controller Unit (MCU) 56. In certain embodiments the MCU 56 executes a choice of either a lossless compression 78 or lossy compression 77 on the x-ray image data reducing its size further. Example of lossless compression 78 is the "JPEG-LS" algorithm achieving a compression ratio of 1:2.23. Example of lossy compression 77 is the "JPEG Quality 80" algorithm achieving a compression ratio of 1:4.23. Following the compression or during the compression the x-ray image data is temporarily and optionally stored block by block in an external memory 52 and transmitted via the radio block 55 (transceiver) to the base station 5, a tablet 7 or a mobile phone device 8. For example using the lossy compression 77 executed on the MCU 56 the transmission time in the example given above would be further reduced to 7 seconds/4.23, i.e. to a mere 1.65 seconds. This is practically real time imaging. This is a remarkable accomplishment if one considers that even wired modern intraoral sensors require today 1-5 seconds for sending via the wired link and displaying the x-ray image.

In an alternative embodiment, that can be combined with the bit truncation and compression described earlier, the MCU 56 executes an algorithm to allow image transmission via the wireless link in parts. In one embodiment the MCU 56 executes the algorithm to choose every second row or every second column, compress via a lossless compression 78 algorithm and transmit via the wireless link. In this way a preview is available in ½ the time what would normally take to send a full image. Even more preferably the MCU 56 executes an algorithm to choose every third or every fourth row or column, compress with a lossless compression 78 algorithm and transmit via the wireless link. In this way the first preview is available in ⅓ or ¼ the time it would take if the full image were to be transmitted. The complete image is therefore sent over in three cycles or in four cycles, while the initial preview is readily available in ⅓ or ¼ the time. For a dental practise this is essential as the doctor or the hygienist can be certain that the exposure succeeded and is able to reposition the sensor immediately after the initial preview while the rest of the image is being sent over. In certain embodiments sufficient storage memory 52, external to the MCU 56, is provided on the further substrate 11 (depicted as 32 in FIGS. 1a and 1b) of the wireless intraoral sensor 1 for safety. Memory cells (32, 52) hold the x-ray image data or at least part therefrom until the wireless link via radio block 55 has successfully transmitted the x-ray image data to the base station, tablet or mobile device. In the unlike event that the wireless link is lost during transmission, the x-ray image data (or at least part of the x-ray image data or certain blocks therefrom) can be re-transmitted because it is safely stored on the memory 52 or the user can always plug the sensor 1 to its base station 5 and download the x-image data from memory 52.

Furthermore in accordance with certain embodiments the truncation and the compression are selective processes. In other words the manufacturer or even the user can determine to apply one or the other or both. Additionally the bit truncation which is now shown to be happening inside the readout ASIC 520, may well take place also inside the MCU 56. Reversely the compression 77 or 78 may be implemented with digital logic inside the readout ASIC 520. These are implementation choices all of which can be tuned by the manufacturer with variations and permutations all falling under the scope of the features of the invention and/or its embodiments.

Figure 8:
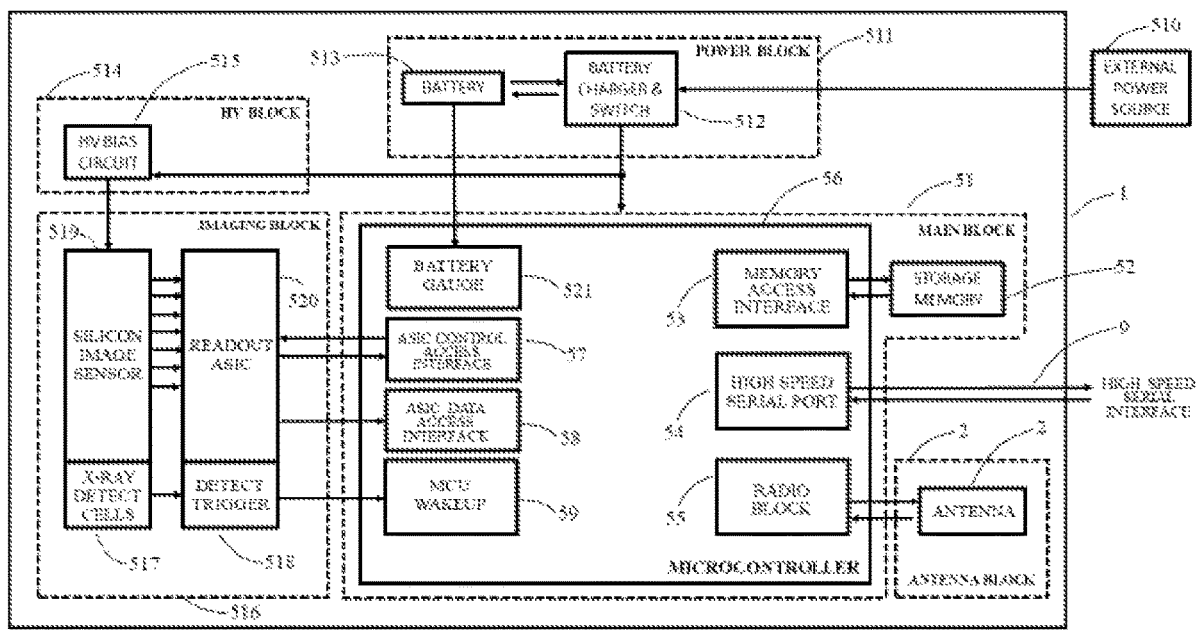
FIG. 8 shows a block diagram of the functional elements of the wireless intraoral sensor in accordance with certain embodiments.

With reference to FIG. 8 there is provided a general block diagram of the novel wireless intraoral x-ray imaging sensor and its structural elements. The wireless intraoral x-ray imaging sensor comprises a) an imaging block 516, b) a Main block 51 comprising a Micro Controller Unit (MCU) block 56 and a storage memory block 52, c) an antenna block 2, d) a power block 511 and in the case of the direct conversion sensor of FIG. 1a, an e) High Voltage (HV) block 514. In the case of direct conversion sensor of FIG. 1a, the imaging block 516 comprises a silicon image sensor 519 for directly converting incoming x-ray events to an electronic signal bonded to a readout substrate block 520 (12 in FIG. 1a). In addition to other functionality described the readout substrate 520 contains event trigger cell circuitry 518 for identifying the beginning of an incoming x-ray exposure. The silicon detector substrate 519 has corresponding trigger detector cells 517 outputting their signal to the trigger cells 518 on the readout substrate 520. The HV bias circuit 515 is for example a booster raising the voltage of the battery 513 in the battery block 511 from 3 V-5 V to 50 V-150 V, suitable to generate appropriate electric field inside the silicon direct conversion detector. The battery charger and switch block 512 is in communication via recharging contacts 22 of FIG. 1a to an external power source 510. Battery gauge 521 in the MCU 56 block monitors the level of battery capacity remaining. Within the MCU 56 there are sub-blocks: 57 for ASIC controlling and access interface, 58 for ASIC data access interface, 59 for waking up the MCU, 53 memory access interface for interfacing with the external storage memory, 54 a high speed serial port for high speed serial interface which is particularly useful for uploading new firmware to the MCU 56 or for reading the content of the external storage memory 52 and radio block 55. Antenna (2, 310) is external to the MCU 56. In accordance with certain embodiments a single MCU 56 hardware device has a plurality and preferably all of the structural elements depicted in FIG. 8 under the Microcontroller block 56, making the sensor especially compact and easy to encapsulate. To that effect the antenna 2, is of the printed antenna 310 kind or a compact ceramic based antenna, incorporated on the PCB surface, i.e. 11 in FIGS. 1a and 1b. Therefore the only component on the further substrate 11 of FIG. 1a (or 1b) that extends laterally and outwards from the further substrate (is the PCB or ceramic) surface 11 is the battery source 30. The singular MCU 56 hardware is responsible for a plethora of functions and functionalities including the management, control and readout of the CMOS ASIC 520, the execution of compression image algorithms, the establishing of wireless link at the 2.4 GHz band and communication with the antenna and the management of the external storage memory 52 for safe keeping the entire compressed image or at least a part of the compressed image with the rest of the image kept in the smaller inherent memory of the MCU. The singular MCU 56 hardware also includes a low power management system integrated therein. All of these elements are combined in one hardware device, the MCU block 56 to make the wireless sensor more compact and more reliable.

Figure 6:
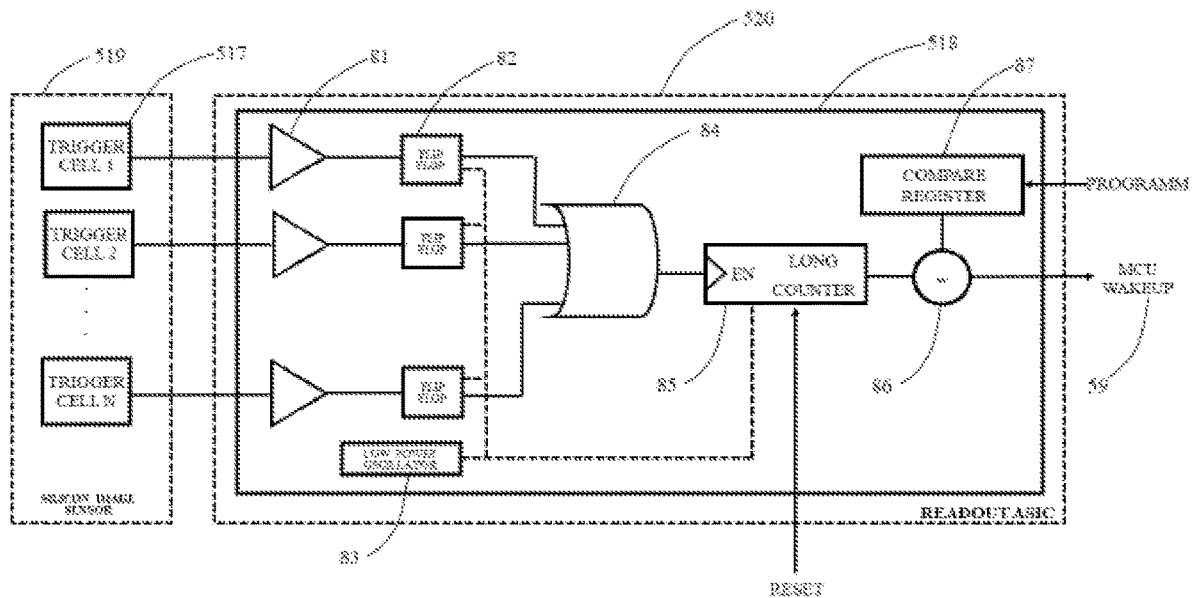
FIG. 6 shows a flow chart of the self-triggering operation and wake up of the microcontroller unit of the wireless intraoral sensor in accordance with certain embodiments.

With reference to FIG. 6 event trigger cells 517 are incorporated on the silicon image sensor 519 and are connected to corresponding readout cells provided on the readout substrate 12 of FIG. 1a. In this embodiment the readout substrate comprises a readout ASIC 520 containing operational amplifiers 81, flip-flops 82, logical gate 84, a low power oscillator 83, a counter 85, a compare register 87 and a trigger gate 86. If enough single events are passing through the silicon trigger cells 517 and the logical operation on gate 84 creates an enabling signal incrementing counter 85 up to the point that it exceeds a preset threshold in the register 87, then gate 86 will send a trigger signal to wake up the MCU 56, which prior to that is in sleep mode.

Figure 7:
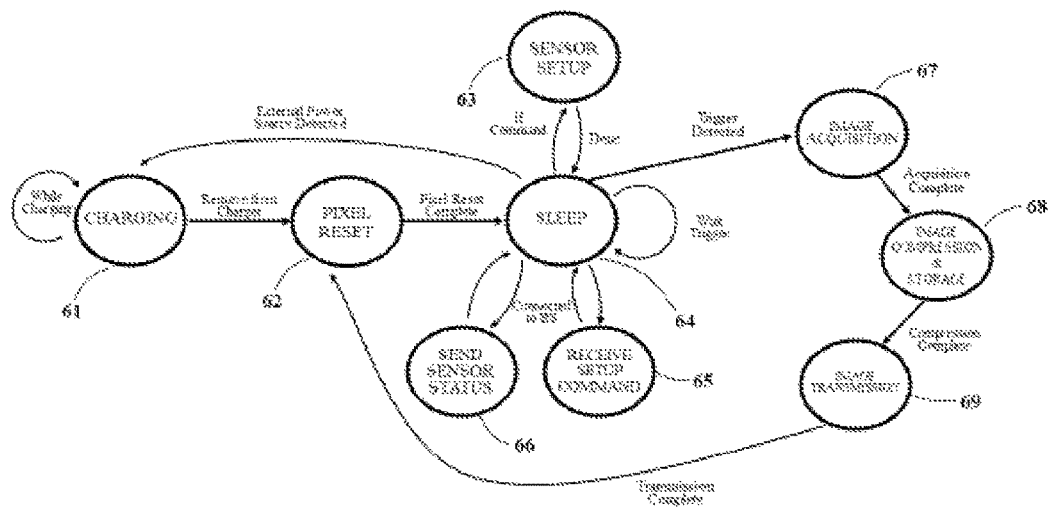
FIG. 7 shows a functional block diagram of the self-triggering, power management and functionality flow of the wireless intraoral sensor in accordance with certain embodiments.

This sequence of events is schematically shown in FIG. 7. While at the charging station 61, the wireless intraoral sensor is charging its rechargeable battery. Upon removal from charger the pixel array is being reset globally and enter sleep state where it is kept at a continuous reset state. In the sleep state the sensor waits for a trigger signal generated as explained with reference to FIG. 6. Once the trigger signal is detected the MCU exits the sleep state and enters the image acquisition state 67 where it stays for a predetermined period of time. For example 500 msec would cover practically all types of exposures. Alternatively the MCU 56 may wait for end of exposure trigger. After the image acquisition is complete the bit truncation and/or image compression 68 and/or sending the image in 2, 3 or 4 parts as described earlier takes place. This operation takes place either on the ASIC readout substrate itself or on the MCU 56 or on both; for example it is convenient and efficient to execute the bit truncation on the readout substrate (ASIC) 520 of FIG. 6 and the image compression as well as earmarking ½, ⅓ or ¼ of the image on the MCU 56. The compressed image is stored on the external memory blocks 52 and transmitted then via the wireless link 69 to the base station which includes a receiver. Once the transmission is complete the pixel array is reset and the MCU 56 enters again the sleep state until a new trigger is detected or until it is placed on the base station for charging.

In accordance with certain embodiments it is to be noted that "sleep" state refers to the state where most of the blocks in FIG. 8 are still active, including MCU block 56 and within that radio block 55, power block 511, imaging block 516, however with a very diminished duty cycle. In sleep state the total current requirement of the intraoral sensor (without of course the base station) is 2.5 mA or less. If, however no triggering event is received within a factory determined timeout period, then the intraoral sensor (but not the base station) goes to what we call the "shutdown" mode. The factory determined timeout period is for example 90 seconds, but typically can practically be from 10 seconds to 10 minutes. In an alternative embodiment the timeout period is set by the user, via for example a command in the software running on the PC. That timeout period is set in the software and then via the base station is communicated to the sensor. User controlled timeout period can be from 10 seconds to 10 minutes or more.

In shutdown mode most components or blocks in FIG. 8 are powered off or are inactive with the exception of the power block 511 and the radio block 55, both of which are running a very low duty cycle. In shutdown mode the current requirement is 1 mA or less. If the user decides that he or she wants to use the sensor he can either place the sensor back to the base station or very practically can put the sensor from the shutdown mode to the sleep mode with a software command issued on the PC. The command is transmitted to the base station and from there via wireless link to the radio block 55. Within less than two seconds, the sensor can go from the shutdown mode to the sleep mode and the operations continue as described above. The great benefit with this dual energy saving architecture is that in sleep mode the sensor is consuming very low power but is ready to take exposures with the self-triggering activating full duty cycle as necessary on the various blocks and in shutdown mode the sensor is consuming extremely low power but is still able to wake up from the shutdown mode and go to the sleep mode within 2 seconds from where it is again available for use. All this without returning to the base station. This architecture provides for very versatile and flexible workflow in a dental practice according to the desires and habits of each dental office. In a preferred embodiment Bluetooth 5.0 or higher is used and one is able to achieve current consumption in the sleep mode of 1.5 mA or less and current consumption in the shutdown mode of 0.2 mA or less. With such miniscule current requirements, the intraoral sensor combined with the battery described earlier can be off base station and ready to use for several days. Furthermore, in this preferred embodiment, while in shutdown mode the intraoral sensor is operating its Bluetooth 5.0 (or higher) transceiver and hence the sensor is discoverable or locatable by any other Bluetooth compatible device. This allows misplaced wireless intraoral sensors to be found within the dental office effortlessly.

It is to be noted that in accordance with certain embodiments at least two of the operations of a) bit truncation; b) image compression, c) at least partial image storage to external memory blocks and d) image transmission in whole or in 2, 3 or 4 parts are processes that can partially overlap or happen in parallel to speed up image transmission and minimize the time from exposure to display.

This is described with reference to FIG. 9, which is a functional flow chart of the operations on a wireless intraoral x-ray imaging sensor in accordance with certain embodiments. After the image is acquired then it is read out block by block. In this context a block of the image means a part of the image either in terms of certain number of pixels in the matrix or in terms of a line, several lines, row or several rows. As one block is read out another block is being bit truncated and compressed. Then there are few alternative to the process on the wireless intraoral sensor. The bit truncated and compressed block is stored in the memory and the next block gets processed, i.e. bit truncated, compressed and stored in the memory. This continues until all blocks have been stored in the memory, i.e. the whole image has been bit truncated, compressed and stored in the memory. This is described in the first flow chart. Subsequently the image that is stored is read out block by block from the memory and gets transmitted block by block via the wireless link.

Figure 9:
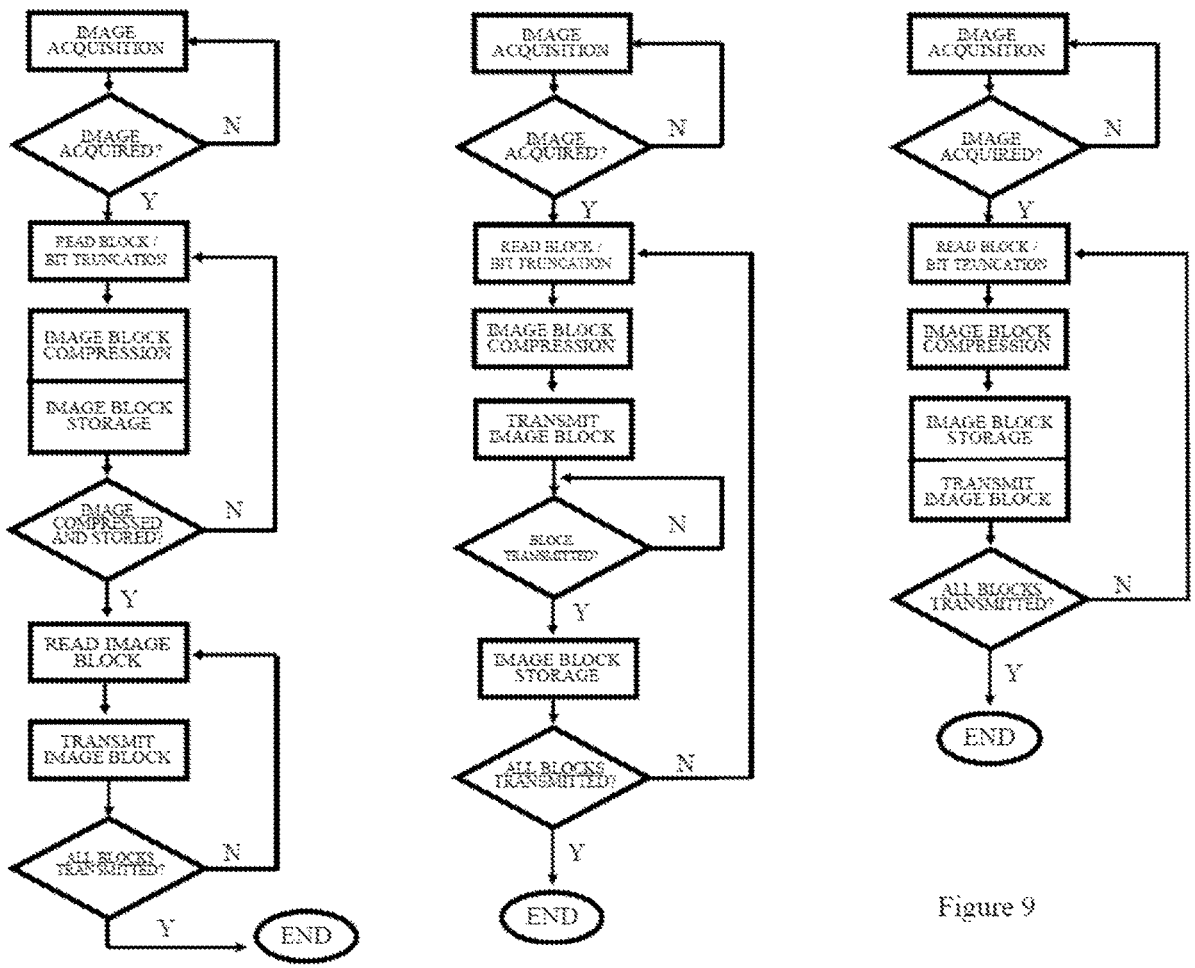
FIG. 9 shows a flow chart of the functions performed in a wireless intraoral sensor in accordance with the various embodiments of certain embodiments.

In an alternative scenario as described in the second flow chart of FIG. 9, after the image block bit truncation and bit compression the image block is being transmitted via the wireless link and upon successful transmission of the image block it is then (the specific block) stored in the memory. The sequence ends after all image blocks have been successfully transmitted and subsequently stored in the memory for safety.

In a third process flow scenario after image block bit truncation compression the block is stored and only then the block is transmitted immediately afterwards. When all blocks have been transmitted in accordance with this process flow, the sequence ends. It is to be understood that some of the process steps may be skipped or exchanged without departing from the scope of features of the invention and/or its embodiments. For example the bit truncation can be skipped and only image block compression can be implemented. Alternatively bit truncation maybe sufficient and image block compression can be skipped. Similarly, the memory storage is a useful but not a necessary step.

Looking again at FIG. 1a it is also to be noted that when the sensor is placed on its base station the contacts 22 act for recharging the battery block 30, as well as offer a path to download the image stored in the memory blocks if needed or upload firmware onto the MCU 31.

The foregoing description has provided by way of non-limiting examples of particular implementations and embodiments of the invention a full and informative description of the best mode presently contemplated by the inventors for carrying out the invention. It is however clear to a person skilled in the art that the invention is not restricted to details of the embodiments presented above, but that it can be implemented in other embodiments using equivalent means without deviating from the characteristics of the invention.

Furthermore, some of the features of the above-disclosed embodiments of this invention may be used to advantage without the corresponding use of other features. As such, the foregoing description should be considered as merely illustrative of the principles of the present invention, and not in limitation thereof. Hence, the scope of the invention is only restricted by the appended patent claims.

The invention claimed is:

1. A wireless intraoral x-ray imaging sensor, comprising:
   a radiation sensitive detector configured to detect impinging x-rays and create an output signal;
      a plurality of pixels on a readout substrate, the plurality of pixels configured to receive said output signal from the radiation sensitive detector, said readout substrate configured to output x-ray image data in the form of analog or digital pixel values; and
   an additional substrate connected to said readout substrate, the additional substrate comprising
      electronics configured to create a wireless link and to transmit said x-ray image data to a receiver, and
      a rechargeable battery configured to provide power to said wireless intraoral x-ray imaging sensor, said rechargeable battery comprising edges that have a minimum distance of 2 mm from the edges of said additional substrate.

2. The wireless intraoral x-ray imaging sensor according to claim 1, wherein said rechargeable battery has a cylindrical shape.

3. The wireless intraoral x-ray imaging sensor according to claim 1, wherein said rechargeable battery is configured to be recharged via contacts provided on the surface of said additional substrate, said contacts having a height profile of less than or equal to 10 mm.

4. The wireless intraoral X-ray imaging sensor according to claim 3, wherein said contacts do not extend beyond the surface of an encapsulation back cover.

5. The wireless intraoral x-ray imaging sensor according to claim 1, wherein said additional substrate comprises a printed antenna.

6. The wireless intraoral x-ray imaging sensor according to claim 1, wherein said wireless electronics comprise a microcontroller which includes control electronics.

7. The wireless intraoral x-ray imaging sensor according to claim 6, wherein said additional substrate comprises memory cells configured to store at least part of the image data, the memory cells being external to the microcontroller.

8. The wireless intraoral x-ray imaging sensor according to claim 1, wherein said readout substrate or the additional substrate includes logic configured to execute bit truncation or data compression.

9. The wireless intraoral x-ray imaging sensor according to claim 6, wherein said microcontroller is configured to execute an algorithm for bit truncation or data compression.

10. The wireless intraoral x-ray imaging sensor according to claim 8, wherein said data compression comprises lossless data compression.

11. The wireless intraoral x-ray imaging sensor according to claim 8, wherein said data compression comprises lossy data compression.

12. The wireless intraoral x-ray imaging sensor according to claim 6, wherein said readout substrate includes event trigger cells and digital logic which are configured to provide a signal to activate a microcontroller wakeup block and wake up the microcontroller from a sleep state upon detection of a start of an exposure.

13. A method for performing wireless intraoral x-ray imaging, said method comprising: providing the wireless intraoral x-ray imaging sensor of claim 1;
   detecting x-rays impinging on the radiation sensitive detector and creating an output signal, receiving said output signal from the detector, and outputting the intraoral x-ray image data from the readout substrate in the form of analog or digital pixel values;
   transmitting said output x-ray image data from the wireless link to the receiver; and two or more of:
   (i) performing bit truncation of the output intraoral x-ray image data prior to transmitting the output x-ray image data from the wireless link, (ii) compressing the output intraoral x-ray image data prior to transmitting the output x-ray image data from the wireless link, (iii) storing at least part of acquired intraoral x-ray image data in a memory provided on said additional substrate prior to transmitting the output x-ray image data from the wireless link, and (iv) storing at least part of the output intraoral x-ray image data in the memory provided on said additional substrate after transmitting the output x-ray image data from the wireless link.

14. The wireless intraoral x-ray imaging sensor according to claim 1, wherein said rechargeable battery is configured to be recharged wirelessly.

15. The wireless intraoral x-ray imaging sensor according to claim 14, wherein said wirelessly rechargeable battery is configured to be recharged utilizing a coil disposed on top of the wirelessly rechargeable battery.

16. The method for performing wireless intraoral x-ray imaging of claim 13, further comprising executing logic or an algorithm to send the intraoral x-ray image data in parts via the wireless link to a base station, a tablet, or a mobile phone providing a fast image preview on a display media in three seconds or less from an end of an exposure.

17. The method for performing wireless intraoral x-ray imaging of claim 16, wherein the sending the image in parts comprises regularly sending every third or every fourth row or column of the image, until all of the rows or columns are sent.

18. The wireless intraoral x-ray imaging sensor according to claim 1, wherein said readout substrate is disposed directly onto a first face of the additional substrate and said rechargeable battery is disposed directly onto a second face opposite to the first face of said additional substrate.

19. The wireless intraoral x-ray imaging sensor according to claim 1, wherein the readout substrate is a Complementary Metal Oxide Semiconductor (CMOS).

* * * * *